US005415161A

United States Patent [19]

Ryder

[11] Patent Number: 5,415,161
[45] Date of Patent: May 16, 1995

[54] INTERMITTANT DEMAND AEROSOL CONTROL DEVICE

[76] Inventor: Steven L. Ryder, 1334 W. Woodcrest Ave., Fullerton, Calif. 92633

[21] Appl. No.: 121,746

[22] Filed: Sep. 15, 1993

[51] Int. Cl.[6] .............................................. A61M 11/00

[52] U.S. Cl. .......................... 128/200.23; 128/200.14; 128/200.16; 310/321

[58] Field of Search ....................... 128/200.24, 200.14, 128/200.16, 200.23, 912, 202.21; 424/202, 204; 116/137 R; 73/861.21, 861.23; 181/141; 310/321; 340/384.6

[56] References Cited

U.S. PATENT DOCUMENTS

| | | | |
|---|---|---|---|
| 2,376,971 | 5/1945 | Kleit | 128/203.25 |
| 2,638,096 | 5/1953 | Waldhaus | 128/202.22 |
| 3,600,612 | 8/1971 | Beeken | 310/322 |
| 3,802,417 | 4/1974 | Lang | 128/716 |
| 3,970,987 | 7/1976 | Kolm | 367/135 |
| 4,054,134 | 10/1977 | Kritzer | 128/205.24 |
| 4,648,393 | 3/1987 | Landis | 128/200.23 |
| 5,042,467 | 8/1991 | Foley | 128/200.23 |
| 5,063,922 | 11/1991 | Häkkinen | 128/200.16 |
| 5,083,560 | 1/1992 | Tillery, Jr. | 128/205.23 |
| 5,201,322 | 4/1993 | Henry et al. | 128/719 |

FOREIGN PATENT DOCUMENTS

| | | | |
|---|---|---|---|
| 178925 | 4/1986 | European Pat. Off. | 128/200.16 |
| 625683 | 1/1935 | Germany | 116/137 R |
| 1051767 | 12/1966 | United Kingdom | 116/137 R |

*Primary Examiner*—Edgar S. Burr
*Assistant Examiner*—William J. Deane, Jr.

[57] ABSTRACT

A T connection mouthpiece comprised of a first tubular member with open ends and internal, a tubular member with a smaller diameter having closed ends to define an air chamber. Proximate to the closed end of the air chamber and distal to the mouthpiece is an aperture. A second tubular conduit opens into the first tubular member to be attached to a nebulizer. On the external surface of the T connection mouthpiece and contiguous with the air chamber, is adhered a thin film of polyvinylidene flouride. When the patient inhales through the T connection, airflow is directed to the aperture to generate a fundamental tone, the acoustical energy is converted to electrical energy by the polyvinylidene flouride film. The electrical signal is received and processed by the electronic circuitry which energizes a solenoid valve normally closed to open and to allow for pressurized gas flow to activate the nebulizer. The aerosol is delivered synchronously during the inspiratory phase of the respiratory cycle. At the end of inspiration, the flow through the T connection has ceased and thus no electrical signal. The solenoid valve returns to the normally closed condition to stop the pressurized gas flow and automatically deactivating the nebulizer.

10 Claims, 2 Drawing Sheets

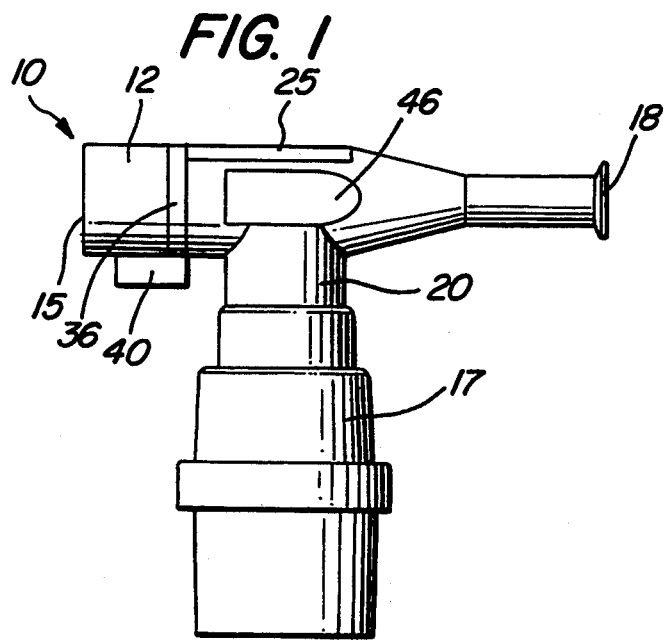
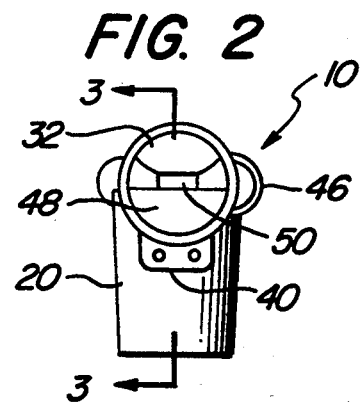
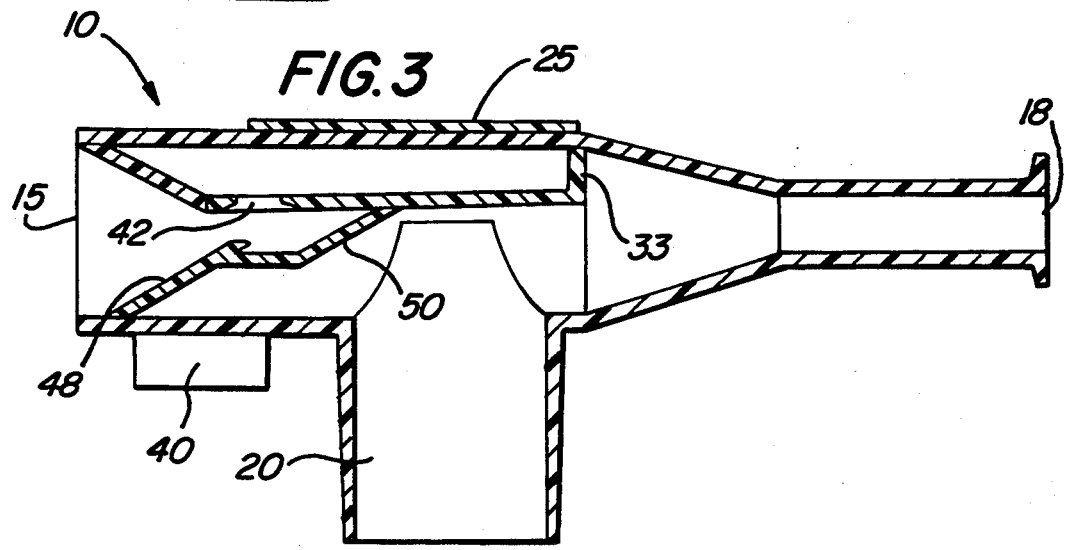
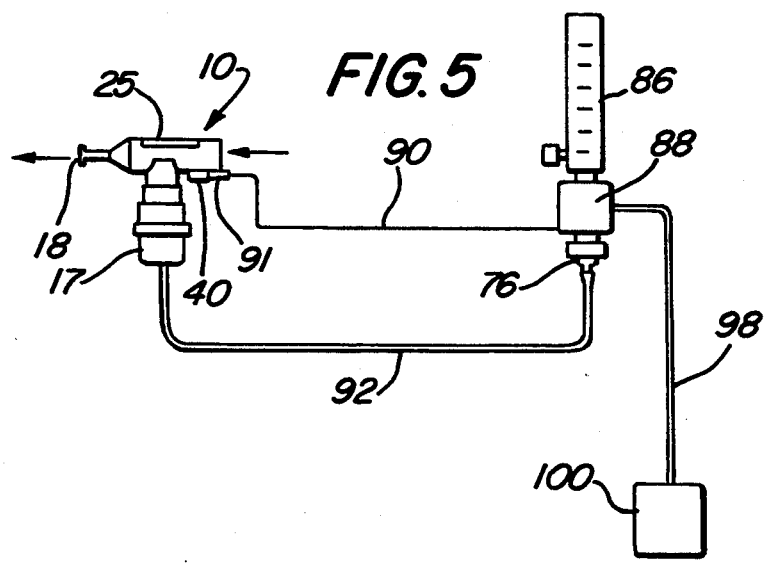

INTERMITTANT DEMAND AEROSOL CONTROL DEVICE

FIELD OF THE INVENTION

This invention relates generally to an apparatus to intermittantly control on inspiratory demand the delivery of an aerosolized medication into the lungs of the patient.

BACKGROUND OF THE INVENTION

Studies have revealed that the current methods of administering a prescribed amount of aerosolized medication via a continuous, pneumatically operated jet nebulizer, will only provide a small percentage of the drug to be deposited in the lungs of the patient.

In the usual manner, the prescribed medication is instilled into the nebulizer and fitted with a mouthpiece and T connection. The nebulizer is connected to a compressed gas source and flow meter, and the flow rate is adjusted sufficiently to create an aerosol.

The patient is instructed to inhale through the mouthpiece and T connection at an inspiratory flow rate necessary to deliver and to maximize the quantity of the aerosolized medication to the lungs, then passively exhale through the mouthpiece and T connection. This procedure is continued until the nebulizer no longer produces a visible aerosol.

An obvious shortcoming of the above therapeutic modality is that during the intervals when the patient is not inhaling through the mouthpiece, the nebulizer will continuously generate an aerosol during therapy, resulting in a substantial loss of medication.

In the hospital, compressed oxygen is predominately utilized to operate small volume jet nebulizers continuously during the course of therapy. Therefore, there is substantial wastage of oxygen.

The continuous aerosol produced increases the risk of occupational and anybody present within the immediate environment, exposure to medication and infectious agents.

At the present to meet the problems and limitations, a simple finger tip control valve is attached below the nebulizer and inline with the connection tube between the nebulizer and the pneumatic source or compressor.

Normally open, the flow is diverted out of the T valve due to the path of least resistance and the jet nebulizer is deactivated. To activate the nebulizer, the patient by manual means will occlude with the thumb the opening of the T valve to cause flow to be diverted to the jet of the nebulizer to generate an aerosol.

In order to benefit from this procedure, the patient must simultaneously coordinate an inspiratory effort with the manual thumb occlusion of the T control valve. Then promptly release the thumb from the valve at the end of the inspiratory effort, then exhale. The inherent difficulty is the requirement of good hand-lung coordination and patient compliance.

This technique does not assure a decreased wastage of medication and is greatly dependent upon whether the patient effectively releases the thumb from the T control valve at the appropriate intervals, therefore potentially reducing the availability of the aerosolized drug to be deposited in the lungs.

U.S. Pat. No. 4,396,015 issued to Johnson sets forth a MEDICATION CONTROL DEVICE FOR USE IN TREATING LUNGS, having an airway device with a tubular section extending into the first passage for communicating with the negative air pressure sensing port of a positive pressure breathing machine which upon sensing will actuate the nebulizer during the inspiratory phase of each breathing cycle.

This device requires the bulky use of an antiquated breathing machine intended for intermittent positive pressure and therefore inconvenient to operate for routine nebulization.

While the foregoing described devices are representative of the prior art to provide a means of intermittant nebulization, there remains nonetheless a continuing need in the art for an improved and effective intermittant aerosol delivery device.

SUMMARY OF THE INVENTION

Accordingly, it is a general object of the present invention to provide an improved intermittant control device for administering an aerosolized drug, which offers convenience of use, disposable sensor, to deliver an aerosol synchronous with the inspiratory phase, and to assist the patient to provide a proper inspiratory flow rate necessary for good aerosol particle penetration and deposition into the lung.

In accordance with the present invention, a T connection having a first tubular member is opened at one end to the atmosphere, the opposite end is intended for the patient to inale and exhale therethrough the T connection.

A second passageway opens into the first tubular member and is connected by friction fit to the outlet of a small volume jet nebulizer. The nebulizer wherein is added a quantity of liquid medication is connected to a pneumatic source, thereby when positive pressure is applied to the nebulizer, the liquid medication is aerosolized.

Internal and within the upper region of the first tubular member, a tubular section with a smaller diameter extends the length of the first tubular member, and is constructed to produce a slight audible sound or tone during the inspiratory flow of air through the T connection.

The vibrating column of air within the smaller tubular section with essentially one open end and a closed end, and therefore an antinode to node respectfully, the length of the smaller tubular section is one-fourth the fundamental wavelength and the fundamental frequency can be calculated and known.

A transducer consisting of PVDF film (polyvinylidene flouride) is adhered to the top external surface of the T connection.

The properties of the PVDF film are piezoelectric and thus an electrical signal is generated as a result of the resonance and vibration of sound.

When the patient inhales through the T connection, the PVDF transducer, senses the slight vibration of sound. The PVDF film connected to an electronic circuit, amplifies and processes the signal to control the on and off switching of a solenoid valve. The solenoid valve controls the flow of the pressurized gas source to activate the nebulizer during the inspiratory phase. At the end of the inspiratory phase, the flow has ceased through the T connection resulting in no vibration of sound and the nebulizer is deactivated. The patient exhales passively through the T connection with no generation of sound.

Thus, the nebulizer is activated synchronously and only during the length of time of the inspiratory phase of the respiratory cycle.

BRIEF DESCRIPTION OF THE DRAWINGS

The features of the present invention, which are believed to be novel, are set forth with particularity in the appended claims. The invention, together with further objects and advantages thereof, may be best understood by reference to the following description taken in conjunction with the accompanying drawings, in several figures of which like reference numerals identify like elements and in which:

FIG. 1 sets forth a side view of the T connection, mouthpiece in accordance to the present invention, attached to a typical small volume, jet nebulizer.

FIG. 2 sets forth a front view of the T connection, mouthpiece of FIG. 1 of the present invention.

FIG. 3 sets forth a section view of the present invention taken along section lines 3—3 in FIG. 2.

FIG. 4 sets forth a schematic block diagram and electrical circuit used for receiving the signal from the PVDF film transducer in FIGS. 1 and 3.

FIG. 5 sets forth a schematic view useful for describing the operation of the invention.

FIG. 6 sets for another schematic view useful for describing the operation of the invention.

DETAILED DESCRIPTION

FIG. 1 sets forth a side view of the T connection, mouthpiece constructed in accordance with the present invention and generally referenced numeral 10. Also shown is the attachment of a small volume, jet nebulizer 17 to demonstrate how the device is typically used.

The T connection 10 includes a first tubular member 12 and is opened at one end 15 to the atmosphere and an opposite end 18 for the patient, whereby a seal is maintained with the mouth to inhale and exhale freely and passively therethrough the first tubular member 12.

The second conduit 20 provides an input fitting to the nebulizer 17, wherein the liquid medication is aerosolized, and is a pathway for aerosol particles into the first tubular member 12 to be inhaled by the patient.

Other external features of the T connection 10 is the orientation of the PVDF film transducer which is adhered to the external top surface of the first tubular member 12 with double sided adhesive tape or epoxy.

The electrical connection on the top and bottom surface of the PVDF film transducer 25 is provided by an adhesive electronic copper tape 36 which has been previously soldered to a miniature two lead electrical plug adaptor.

Of the middle lateral aspect of the first tubular member 12 is a window opening 46 to decrease the resistance of the inspiratory and expiratory flow, and its complete function will be later explained.

FIG. 2 sets forth an illustration of the front view of the T connection mouthpiece. 10 and front view of the internal structures. These internal structures are better appreciated in the sectional view of FIG. 3.

Referring now to FIG. 3, a semicircular tubular section 32 having a smaller radius, extends the length within the upper internal region of the first tubular member 12. The distal end of the semicircular tubular section 32, near the open end 15 has a small aperture 42 and a closed opposite end 33.

A semicircular plate or planar surface projection 48 having a diameter less than half of the internal diameter of the first tubular member 12, is positioned to direct the inspiratory flow of atmospheric air over the small aperture 42.

Therefore, as the patient inhales through the T connection 10, the inspired airflow being directed by the semicircular plate over the small aperture 42, which will cause the enclosed column of air within the semicircular tubular section 32 to vibrate, and the generation of a tone.

Respectively, there is an antinode to node relationship in the vibrating column of air with one-fourth the wavelength. The length of the semicircular tubular section 32 from the small aperture 42 to the closed end 33 is 3.25 inches, and the fundamental wavelength is $4 \times 3.25$ inches or 1.08 feet. Therefore, the fundamental frequency or tone assuming the speed of sound in the ambient air is 1100 feet/second, is 1,015 vibrations/-second.

The PVDF film transducer 25 has piezoelectric properties and during the inspiratory flow, the mechanical vibration of the sound and resonating column of air from the semicircular tubular section 32 is converted to an electrical signal.

The signal thus generated from the PVDF film transducer 25 is interfaced to an electronic circuit via the electronic copper tape 36 to the minature two lead electrical plug adaptor 40.

A rectangular plate 50 is positioned midline and internal of the first tubular member 12, and part of the complete unit of the semicircular plate or planar surface projection 48.

The size of the rectangular plate 50 is small enough to allow for a minimum resistance to the inspiratory and expiratory flow, and large enough to inhibit flow over the aperture 42 during the passive exhalation through the T connection 10 and preventing an audible tone.

As previously mentioned, the window opening 46 on the T connection 10 in FIGS. 1 and 2 not only reduces the airflow resistance, but also governs the rate of the inspiratory flow ultimately therethrough the opened end 15.

Within certain limits, the larger the dimension of the window opening 46, there will be a reciprocal reduction of the inspiratory flow directed over the aperture 42 and therefore a decrease in the intensity of sound during the inspiratory phase.

FIG. 4 sets forth a schematic block diagram of an electrical circuit to receive and process the incoming signal from the PVDF film transducer 25.

The electronic componets are standard and well known in the art.

In general, during the inspiratory phase a fundamental tone of 1 kHz is generated from the T connection 10 which is converted to an electrical signal by the PVDF film transducer 25 and amplified by a high impedance input amplifier 56.

The active filtering stage 60 is comprised of a band pass (@ 1 kHz ), high pass and low pass filters and attenuates any odd harmonics of the fundamental tone, i.e., the first overtone is the 3rd harmonic, second overtone is the 5th harmonic, etc. Also, the filters effectively reduces and removes the noise created by the pneumatically driven jet of the nebulizer 17 which has been transmitted with the fundamental tone by the PVDF film 25. Without a clean signal of the fundamental tone, there is sporadic or no switching by the electronic circuit to turn on and off the solenoid 80.

The clarified analog signal is amplified by the summing amplifier 62, and conducted to the phased locked loop/tone decoder 68 which the freqency of the voltage controlled oscillator has been adjusted to specifically respond to the fundamental tone of 1 kHz. When the loop is locked, the output is at logic 0, this output is converted to a logic 1 via the inverter 70 and the voltage is then conducted to the base of the Darlington pair transistors, switching on and thus energizing the solenoid 80.

Referring now to FIG. 5 is a schematic view illustrating the operation of the invention. This configuration is an example of how the device would be utilized in the hospital or clinic.

Figure 4:
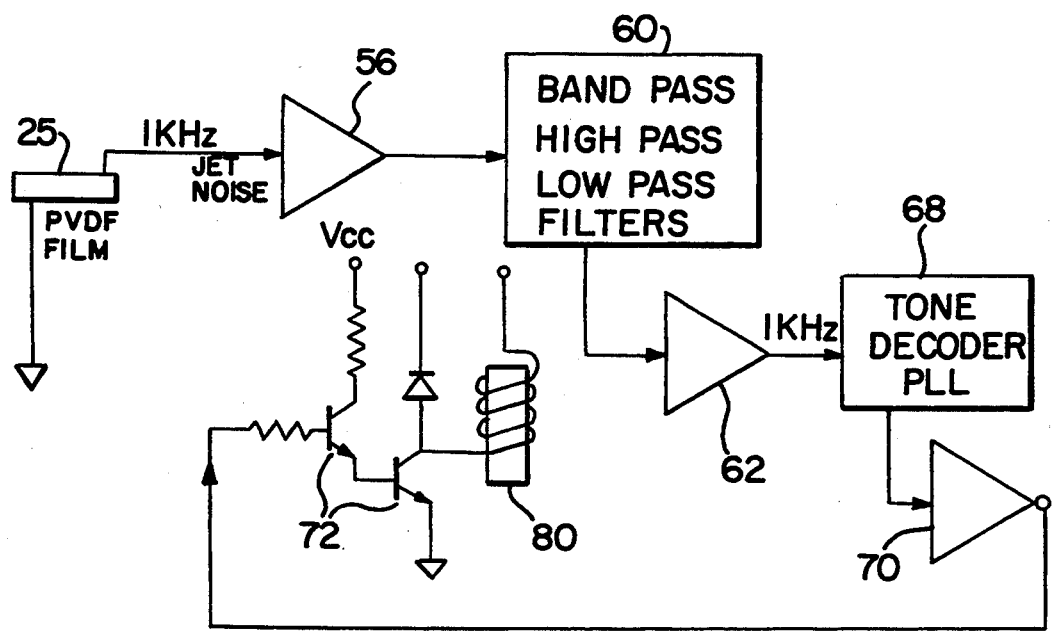

A standard oxygen or compressed air flowmeter (pressure compensated Thorpe tube) 86, is connected to a wall outlet to a piped-in system of pressurized gas source or connected to a compressed gas cylinder.

The solenoid valve unit 88 is threaded onto the flowmeter 86. An electrical connection between the solenoid valve unit 88 to the AC adaptor and the control electronics 100 is by the conducting wires 98.

The small two lead conducting wires 90 are held in place within the housing of the solenoid valve unit 88 and continues along with the conducting wires 98 to the AC adaptor and control electronics 100.

A flexible, vinyl plastic gas supply tube with thread adaptor 76, is threaded onto the solenoid valve unit 88, and the other end of the tube is attached to the nebulizer 17, wherein a quantity of liquid medication is instilled.

The T connection 10 to the nebulizer 17, is held together by a friction fit, and connected to the control electronics 100 by the connection of the miniature two lead electrical plug adaptor 40 and electrical plug adaptor 91, which is attached to the small two lead conducting wires 90.

In operation, the condition of the solenoid valve unit 88 is normally closed, the flow of the flowmeter 86 is adjusted until the plunger float or ball flow rate indicator drops to the bottom of the flowmeter 86. Therefore no pressurized gas flow to the nebulizer 17.

During the inspiratory phase of the respiratory cycle, the patient will inhale on the T connection, mouthpiece 10 at 18. The airflow from the atmosphere therethrough the T connection 10, will cause the fundamental tone to be generated.

The signal is conducted from the PVDF film transducer 25 to the small conducting lead wires 90 to the control electronics 100. The electronic circuitry processes the incoming signal and sends power via the conducting wires 98 to the solenoid valve unit 88, which opens to allow pressure and gas flow to activate the nebulizer 17.

The aerosol delivered occurs instantaneously and synchronously during the length of the inspiratory phase. Immediately, once the inspiratory flow has ceased through the T connection 10, the nebulizer 17 is automatically deactivated. The patient passively exhales through the T connection member 10.

The sensitivity of the electronics is adjusted to assure an average inspiratory flow rate from 0.33 L/s to 0.8 L/s to maximize aerosol deposition into the patients lungs. i.e., if the patient does not inhale through the T connection 10 sufficiently to create the fundamental tone (less than 0.33 L/s), the nebulizer 17 will not be activated. Likewise a forced inspiratory flow rate (greater than 0.8 L/s) through the T connection 10 will cause the apparatus to produce odd harmonics and overtones which are filtered out by the electronic circuitry, and therefore the nebulizer will also not be activated. Clinically, this feature is an important benefit.

Figure 6:
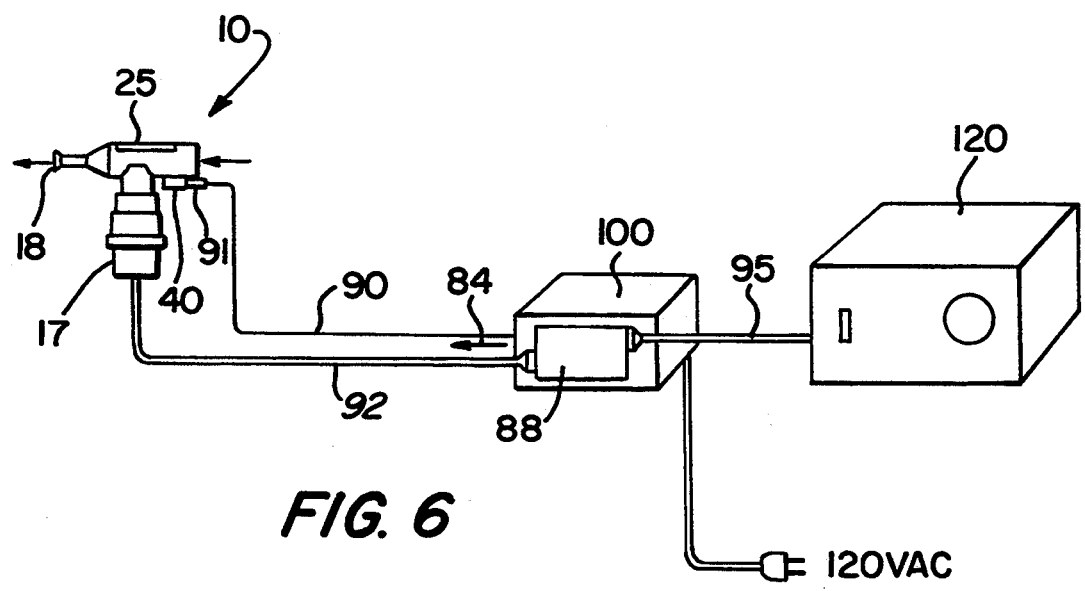

FIG. 6 sets forth another schematic view useful for describing the operation of the invention. This configuration is an example of how the device would be utilized for the homecare patient.

The operation and functional aspects of the T connection, mouthpiece 10, path of signal conduction and electronic circuitry are the same as previously desribed in FIG. 5. The major differences are the control electronics and AC adaptor 100 and the solenoid valve unit 88 are contained as one unit.

A plastic vinyl gas supply tube 95 is connected from the air compressor 120 to the solenoid valve unit 88 and normally open. This will shunt the pressurized airflow to the atmosphere as indicated by arrow 84. The diverted flow will bypass the nebulizer 17 and therefore deactivated and no production of aerosol. When the power is sent from the control electronics 100 to energize the solenoid valve unit 88, the channel (not shown) normally allowing the pressurized airflow to be vented to the atmosphere, is occluded and the pressurized airflow is diverted to the nebulizer 17 via the plastic vinyl gas supply tube 92, producing an aerosol synchronously and during the length of the inspiratory phase of the patient.

While the particular embodiment of the invention has been shown and described, it will be obvious to those skilled in the art that changes and modifications may be made without departing from the invention in its broader aspects. Therefore, the aim in the appended claims is to cover all such changes and modifications an fall within the true spirit and scope of the invention.

I claim:

1. An apparatus for supplying an aerosol in response to an intermittent demand comprising:
   a first tubular member having first and second opened ends for airflow therethrough;
   an internal substantially tubular member contiguous with an internal surface of said first tubular member, said internal substantially tubular member defining an air chamber within the tubular member, said internal tubular member having closed ends and an aperture near one of the closed ends;
   a planar surface projection internal to the first tubular member and external to the internal tubular member, said planar surface projection oriented to deflect airflow in a first direction through said first tubular member toward said aperture of the internal tubular member;
   a second surface projection upstream in said first direction of said internal tubular member and said aperture, said second surface being oriented to prevent airflow in a second, opposite direction from entering said aperture;
   a window in the first tubular member, said window being arranged to entrain additional airflow through said first tubular member thereby changing the rate of airflow through the first and second opened ends; and
   a second tubular conduit perpendicular to and opening into said first tubular member at a point between said opened ends; wherein
   when airflow is effected in said first tubular member, airflow deflected by said planar surface projection through said aperture will generate a vibrational acoustical energy.

2. The apparatus of claim 1 further comprising a piezoelectric element for converting said vibrational acoustical energy into an electrical signal.

3. The apparatus of claim 2, wherein said piezoelectric element comprises polyvinylidene fluoride.

4. The apparatus of claim 2, wherein said piezoelectric element is secured to an external surface of said first tubular member corresponding to the internal contiguous region.

5. The apparatus of claim 2 further comprising an electronic means for receiving and processing said electrical signal.

6. The apparatus of claim 5, wherein said piezoelectric element further comprises electrical connections on each side thereof; said connections being secured to said first tubular member by conductive tape.

7. The apparatus of claim 5, wherein said piezoelectric element further comprises electrical connections on each side thereof; said connections being secured to said first tubular member by epoxy.

8. The apparatus of claim 5, wherein said electronic means further comprises a high impedance input amplifier; band pass, high pass and low pass active filters; and a phase-locked loop tone decoder circuit.

9. The apparatus of claim 8 further comprising a solenoid operatively connected to valve means for selectively admitting into said second tubular member a pressurized gas flow, said solenoid being operatively connected and controlled by said electronic means.

10. The apparatus of claim 9, wherein said valve means further comprises vent means for venting a pressurized gas flow to the ambient.

* * * * *